US010258588B2

(12) United States Patent
Aho et al.

(10) Patent No.: US 10,258,588 B2
(45) Date of Patent: Apr. 16, 2019

(54) CONTROLLED RELEASE FATTY ACID COMPOSITIONS FOR USE IN BODY RECONSTRUCTION AND BODY-SHAPING (71) Applicant: PB&B SA, Lausanne (CH)

(72) Inventors: Anthony Youri Aho, Lausanne (CH); Raghunathan Sandeep, Lausanne (CH)

(73) Assignee: PB&B SA, Lausanne (CH)

( * ) Notice: Subject to any disclaimer, the term of this patent is extended or adjusted under 35 U.S.C. 154(b) by 0 days.

(21) Appl. No.: 15/108,782

(22) PCT Filed: Dec. 30, 2014

(86) PCT No.: PCT/EP2014/079448
§ 371 (c)(1),
(2) Date: Jun. 28, 2016

(87) PCT Pub. No.: WO2015/101625
PCT Pub. Date: Jul. 9, 2015

(65) Prior Publication Data
US 2016/0324817 A1   Nov. 10, 2016

(30) Foreign Application Priority Data

Dec. 31, 2013   (EP) .................................. 13199866

(51) Int. Cl.
*A61K 31/201* (2006.01)
*A61K 8/36* (2006.01)
*A61Q 19/00* (2006.01)
*A61K 8/85* (2006.01)
*A61Q 19/08* (2006.01)
*A61K 8/11* (2006.01)
*A61K 9/50* (2006.01)
*A61K 9/00* (2006.01)
*A61K 9/16* (2006.01)
*A61K 45/06* (2006.01)
*A61K 31/167* (2006.01)
*A61K 31/192* (2006.01)
*A61K 31/277* (2006.01)
*A61K 31/352* (2006.01)
(Continued)

(52) U.S. Cl.
CPC .............. *A61K 31/201* (2013.01); *A61K 8/11* (2013.01); *A61K 8/361* (2013.01); *A61K 8/85* (2013.01); *A61K 9/0019* (2013.01); *A61K 9/1647* (2013.01); *A61K 9/5031* (2013.01); *A61K 31/167* (2013.01); *A61K 31/192* (2013.01); *A61K 31/20* (2013.01); *A61K 31/277* (2013.01); *A61K 31/352* (2013.01); *A61K 31/355* (2013.01); *A61K 31/375* (2013.01); *A61K 31/405* (2013.01); *A61K 31/4166* (2013.01); *A61K 31/427* (2013.01); *A61K 31/4439* (2013.01); *A61K 31/522* (2013.01); *A61K 31/565* (2013.01); *A61K 31/567* (2013.01); *A61K 31/57* (2013.01); *A61K 31/573* (2013.01); *A61K 31/585* (2013.01); *A61K 38/18* (2013.01); *A61K 38/1808* (2013.01); *A61K 38/1825* (2013.01); *A61K 38/1875* (2013.01); *A61K 38/28* (2013.01); *A61K 38/30* (2013.01); *A61K 45/06* (2013.01); *A61L 27/18* (2013.01); *A61L 27/54* (2013.01); *A61Q 19/001* (2013.01); *A61Q 19/08* (2013.01); *A61K 2800/56* (2013.01); *A61K 2800/91* (2013.01); *A61L 2300/22* (2013.01); *A61L 2300/602* (2013.01); *A61L 2430/34* (2013.01)

(58) Field of Classification Search
None
See application file for complete search history.

(56) References Cited

U.S. PATENT DOCUMENTS 5,541,225 A * 7/1996 Leaf ....................... A61K 31/20
514/560
6,559,184 B2 * 5/2003 Neal ..................... A61K 9/0034
514/33
(Continued)

FOREIGN PATENT DOCUMENTS

EP   1581181 A2   10/2005
EP   1581181 B2   10/2005
(Continued)

OTHER PUBLICATIONS

M. Vedamurthy, "Soft tissue augmentation—Use of hyaluronic acid as dermal filler", Cosmetic Dermatology, 2004; 383-387.*
Mao et al., "Facial Reconstruction by Biosurgery: Cell Transplantation Versus Cell Homing", Tissue Engineering: Part B, 2010; 257-262.*
Vedamurthy et al., "Dermal Fillers: Tips to Achieve Successful Outcomes", J Cutan Aesthet Surg., 2008; 64-67.*
(Continued)

*Primary Examiner* — Lianko G Garyu
(74) *Attorney, Agent, or Firm* — Bryan D. Zerhusen, Esq.; Cantor Colburn LLP (57) ABSTRACT The present invention is directed to compositions comprising physiologically acceptable, metabolic lipids, and physiologically acceptable, preferably biodegradable controlled release (CR) compounds, wherein the lipids are cell-free and the CR compounds release the metabolic lipids over a delayed time period under physiological conditions. In addition, the present invention relates to the use of such a composition for producing a cosmetic or therapeutic composition, preferably for fat tissue expansion or fat tissue repair. Also, the invention pertains to a method for the therapeutic or cosmetic treatment of a mammal comprising the administration of the composition of the invention and preferably injecting the composition while withdrawing the injection needle until the tissue area of interest is treated.

27 Claims, 4 Drawing Sheets (51) Int. Cl.
| | |
|---|---|
| A61K 31/355 | (2006.01) |
| A61K 31/375 | (2006.01) |
| A61K 31/405 | (2006.01) |
| A61K 31/4166 | (2006.01) |
| A61K 31/427 | (2006.01) |
| A61K 31/4439 | (2006.01) |
| A61K 31/522 | (2006.01) |
| A61K 31/565 | (2006.01) |
| A61K 31/573 | (2006.01) |
| A61K 31/585 | (2006.01) |
| A61K 31/567 | (2006.01) |
| A61L 27/54 | (2006.01) |
| A61K 38/18 | (2006.01) |
| A61K 38/28 | (2006.01) |
| A61K 38/30 | (2006.01) |
| A61K 31/20 | (2006.01) |
| A61K 31/57 | (2006.01) |
| A61L 27/18 | (2006.01) |

(56) References Cited

U.S. PATENT DOCUMENTS

| | | |
|---|---|---|
| 2006/0073178 A1 | 4/2006 | Giampapa |
| 2009/0169642 A1 | 7/2009 | Fradette |
| 2009/0291066 A1 | 11/2009 | Pappas |

FOREIGN PATENT DOCUMENTS

| | | | | |
|---|---|---|---|---|
| WO | WO 2012/068783 A1 | 5/2012 | | |
| WO | WO 2012097281 A2 * | 7/2012 | ............. | A61K 31/78 |

OTHER PUBLICATIONS

Hudson et al., "Use of Local Anesthesia for Arterial Punctures", American Journal of Critical Care, 2006, pp. 595-599 (Year: 2006).*

Higgins, "IV drug preparation and reconstitution", Nursing Times, 2005; p. 22 (Year: 2005).*

Makadia et al., "Poly Lactic-co-Glycolic Acid (PLGA) as Biodegradable Controlled Drug Delivery Carrier", Polymers, 2011, pp. 1377-1397 (Year: 2011).*

Manning et al., "The Genesis of Arrhythmias during Myocardial Ischemia: Dissociation between Changes in Cyclic Adenosine Monophosphate and Electrical Instability in the Rat", Circulation Research, 1985, pp. 668-675 (Year: 1985).*

Chen et al., "17B-estradiol decreases vulnerability to ventricular arrhythmias by preserving Connexin43 proteins in infarcted rats", European Journal of Pharmacology, 2010, pp. 73-81 (Year: 2010).*

Schlesinger et al., "Albumin inhibits adipogenesis and stimulates cytokine release from human adipocytes", Am J Physiol Cell Physiol, 2006, pp. C27-C33 (Year: 2006).*

Raut et al., "Lecithin organogel: A unique micellar system for the delivery of bioactive agents in the treatment of skin aging", Acta Pharmaceutica Sinica B, 2012; pp. 8-15 (Year: 2012).*

Rose L I et al: "Pathophysiology of spironolactone-induced gynecomastia", Annals of Internal Medicine, American College of Physicians, New York, NY; US, vol. 87, No. 4, Oct. 1, 1977 (Oct. 1, 1977), pp. 398-403, XP009183830, ISSN: 0003-4819.

Holmstrom T E et al: "Differential signalling pathways for EGF versus PDGF activation of Erk1/2 MAP kinase and cell proliferation in brown pre-adipocytes", Experimental Cell Research, Academic Press, US, vol. 314, No. 19, Nov. 15, 2008 (Nov. 15, 2008), pp. 3581-3592, XP025628101, ISSN: 0014-4827, DOI: 10.1016/J. YEXCR.2008.09.007 [retrieved on Sep. 24, 2008].

Jorge M. Tagle et al: "Clinical Performance of a Dermal Filler Containing Natural Glycolic Acid and a Polylactic Acid Polymer Results of a Clinical Trial in Human Immunodeficiency Virus Subjects with Facial Lipoatrophy", Clinical Aesthetic Dermatology, Feb. 28, 2010 (Feb. 28, 2010), pp. 42-47, XP055183937, Retrieved from the Internet: URL:http://www.ncbi.nlm.nih.gov/pmc/articles/PMC2921761/pdf/ jcad_3_2_42. Pdf; [retrieved on Apr. 17, 2015].

International Search Report and Written Opinion for PCT/EP2014/079448, dated May 11, 2015.

Yuksel et al., "Increased Free Fat-Graft Survival with the Long-Term, Local Delivery of Insulin, Insulin-Like Growth Factor-1, and Basic Fibroblast Growth Factor by PLGA/PEG Microspheres", Plastic & Reconstructive surgery, vol. 105(5), Apr. 2000, 1712-1720.

* cited by examiner

CONTROLLED RELEASE FATTY ACID COMPOSITIONS FOR USE IN BODY RECONSTRUCTION AND BODY-SHAPING

RELATED APPLICATION

This application is a National Stage of PCT/EP2014/079448, filed: Dec. 30, 2014 titled: Controlled Release Fatty Acid Compositions For Use in Body Reconstruction and Body-Shaping, which claims the benefit and priority to European Application No. 13199866.8, filed on Dec. 31, 2013, all of which are incorporated by reference in their entirety for all purposes.

The present invention is directed to compositions comprising physiologically acceptable, metabolic lipids, and physiologically acceptable, preferably biodegradable controlled release (CR) compounds, wherein the lipids are cell-free and the CR-compounds release the metabolic lipids over a delayed time period under physiological conditions. In addition, the present invention relates to the use of such a composition for producing a cosmetic or therapeutic composition, preferably for fat tissue expansion or fat tissue repair. Also, the invention pertains to a method for the therapeutic or cosmetic treatment of a mammal comprising the administration of the composition of the invention and preferably injecting the composition while withdrawing the injection needle until the tissue area of interest is treated.

BACKGROUND OF THE INVENTION

Fat tissue stores energy, provides insulation and defines exterior structural features, for example in the face, breasts, buttocks or any other form-defining body parts of mammals. Next to cosmetic desires there are also therapeutic applications for fat tissue engineering and reconstruction, e.g. breast reconstruction after mastectomies, HIV-induced lipid dystrophy and facial reconstruction after trauma.

Traditional methods for treating fat tissue defects and for cosmetic tissue augmentation employ a filling material that replaces or adds volume to the targeted body part. The filling materials are classified as autologous fillers and non-autologous fillers.

Autologous fat transfer, i.e. surgical fat cell isolation from one part and re-injection into another part of the body, has been practiced since the late 19th century. Autologous fat cell transfer to the face has the advantage of its permanent nature and the autologous fat based injections result in a more soft and glowing look of the rejuvenated face. On the other hand, a major drawback is the unpredictability of the results due mostly to varying survival rates of adipose cells after injection. For example, for fat cells injected into fat tissue areas (e.g. face or breasts) 30-70% die, mainly because of the absence of nutrients and oxygen in the pre-angiogenic state. Another problem is the survival of the fat cells during isolation. This issue has been improved by a number of techniques such as the use of aspirated needles and specialized treatment of the isolated fat cells. A further drawback of this technique is that it requires surgical intervention and adequate amounts of autologous fat cell materials, which is not available for many individuals.

A more modern course of action in fat tissue engineering is the injection of adipose derived stem cells (ADSC) that cause proliferation of new adipocytes. However, the process involves a lengthy, complicated and expensive procedure including liposuction, isolation of ADSC from the adipose cells by specialized ultracentrifugation, optionally with the treatment of the isolated ADSCs with differentiating factors, and reinjection of differentiated cells into the desired target tissue.

Because of the cell survival issue of fat cells various non-cellular filler materials were envisaged. Collagen was the most widely used filler in the market till the emergence of hyaluronic acid in 2003. Collagen induces mild immunogenic reactions because of its bovine source and this technology came to an end with the emerging awareness of the risk of bovine spongiform encephalopathy (BSE). Hyaluronic acid (HA) has been used as an off prescription fat tissue filler for years even though it was FDA approved much later in 2003. It has become the most dominant filler on the market. Modern commercial HA is highly crosslinked with divinyl sulfone-based compounds for increased half-life and of recombinant rather than animal source for reducing immunity. The principle drawback of HA is its limited life span after injection. Most HA-based fillers endure for 3 to 12 months only. As with silicon-based implants, the use of HA for breast enhancement can interfere with mammography-based cancer detection. Other potential issues related to HA are a higher frequency and risk of granuloma development, nodule formation and mastalgia, implant palpability, capsular contraction, superficial infections and abscess development.

Local and systemic administration of estrogens has also been known to increase women's breast size by estradiol receptor induction of adipose tissue generation. Spironolactone has been known to induce breast development and feminization due to its anti-androgen properties.

Another approach for the de-novo adipose tissue generation is the long-term local delivery of insulin and insulin-like growth factor-1 (IGF-1) and basic fibroblast growth factor (bFGF) by PLGA/PEG microspheres and this has been tested in an in vivo rat model (Yuksel et al., Plastic & Reconstructive surgery, vol. 105(5), April 2000, 1712-1720), wherein insulin- and IGF-1-containing microspheres were administered directly to the deep muscular fascia of the rat abdominal wall to evaluate their potential for the de novo adipose tissue generation via adipogenic differentiation from non-adipocyte cell pools. The microspheres function as controlled release (CR) compounds that provide for a long-term local delivery of the proteins that induce the de novo generation of adipose tissue at the administration site.

In summary, the prior art techniques for treating fat tissue defects and for cosmetic fat tissue augmentation require either the autologous transfer of fat cells or adipose derived stem cells (ADSC), the local administration of non-cellular non-permanent fillers or, alternatively, the local administration of adipocyte differentiation and growth factors.

It is the objective of the present invention to provide a composition for treating fat tissue defects and for cosmetic fat tissue augmentation that is technically easy to produce and administer, that requires minimal surgical intervention and that is safe and cost efficient.

In a first aspect the problem underlying the present invention is solved by the provision of a composition comprising (i) physiologically acceptable, metabolic lipids, and (ii) physiologically acceptable, preferably biodegradable controlled release (CR) compounds, wherein the metabolic lipids are cell-free and the CR compounds release the metabolic lipids over a delayed time period under physiological conditions.

The term controlled release (CR), as used herein, refers to the technology of formulating active compounds to control the active compounds availability, e.g. a timed release such as for example a sustained (prolonged) release, a pulse release, a delayed release, etc. and combinations thereof. Typical CR applications are fertilizers, cosmetics and pharmaceuticals. CR compounds for use in the present invention are compounds formulated together with said lipids and optionally other physiologically active compounds that delay the release of said lipids and active compounds in comparison to the absence of the CR compounds when administered to a physiological environment, preferably a human body tissue part such as of the face, breasts, buttocks, etc.

The CR compounds and metabolic lipids for use in the invention should be physiologically acceptable, i.e. substantially non-toxic to the treated tissue. It is further preferred that the CR compounds of the invention are substantially biodegradable, i.e. they are removed and preferably metabolized from the administration site with time.

The CR compounds release the metabolic lipids and optionally other active compounds over a delayed time period under physiological conditions. Physiological conditions, as mentioned herein in the context of the invention, are the in vivo conditions at the tissue site of administration, e.g. adipose tissue conditions.

The release profile of the CR compounds for the metabolic lipids and optionally other active compounds is not limited and depends on the formulation of the composition as well as on the target tissue and the mode and frequency of administration. Generally, an initial burst release followed by a steady state release initiate adipocyte growth and/or proliferation while maintaining a physiologically effective level of the metabolic lipids and the optional active compounds desired.

In a preferred embodiment the CR compounds release the metabolic lipids and optionally other active compounds over a delayed time period of 7 days to 12 months, preferably 30 to 90 days, more preferably 50 to 70 days, most preferably over about 60 days.

The metabolic lipids for use in the composition of the invention are cell-free, meaning that they do not form part of living or dead cells and that they are essentially free of cellular components such as membranes, nuclei, nucleic acids, etc. Cell-free metabolic lipids have the advantage that they are less immunogenic, pharmacologically safe and more accessible to absorption by cells such as the cells in the target tissue.

Lipophilicity refers to the ability of a chemical compound to dissolve in fats, oils, lipids and non-polar solvents such as hexane or toluene. The term metabolic lipids as used herein is defined as any compounds that are lipophilic and that can be ingested, stored and metabolized for producing cellular energy, e.g. ATP, by cells, preferably by cells in adipose tissues, more preferably by adipocytes.

The composition of the invention can be locally administered, e.g. by injection, preferably multiple and evenly distributed injections, into tissues for treating fat tissue defects and for cosmetic fat tissue augmentation.

The released metabolic lipids have a number of advantageous effects on the treated tissue. Contrary to isolated cells, e.g. fat cells and ADSC, metabolic lipids are less immunogenic, they do not comprise harmful constituents such as bovine-derived collagen (BSE) and they can be ingested by target cells directly and fast. The direct and advantageous effect of the inventive composition on fat cells and other cells in the target tissue is that these cells are continuously "superfed" leading to increased volume.

To further assist the growth of the target tissue the composition of the invention can comprise further active compounds, preferably fat cell growth effector compounds which will increase fat cells in size and numbers, i.e. stimulate fat cell growth and adipogenesis, i.e. cell differentiation of pre-adipocytes into adipocytes and adipocyte volume growth.

In a more preferred embodiment the composition of the present invention comprises at least one fat cell growth effector, preferably a fat cell growth effector selected from the group consisting of a. insulin, insulin growth factor binding proteins 1 to 7 (IGFBP 1-7), insulin growth factor 1 (IGF-1) and insulin growth factor 2 (IGF-2), preferably insulin, insulin-growth factor 1 (IGF-1) and insulin growth factor 2 (IFG-2), more preferably insulin and insulin-growth factor 1 (IGF-1), most preferably human insulin;

b. fibroblast growth factors (FGFs), preferably FGF-1, FGF-2, FGF-10 and FGF-21, more preferably FGF-1 and FGF-2, most preferably FGF-1;

c. glucocorticoids, preferably selected from the group consisting of cortisol, cortisone, prednisone, prednisolone, triamcinolone, methylprednisolone, dexamethasone and betamethasone, preferably dexamethasone and betamethasone;

d. cyclic adenosine monophosphate (cAMP) activators, preferably selected from the group consisting of aminophylline, pentoxyfilline, theophylline, isobutyl-methylxanthine (IBMX), forskolin and dehydroabietic acid (DAA), preferably aminophylline, pentoxyfilline and theophylline;

e. peroxisome proliferator-activated receptor γ-2 (PPARγ2) agonists, preferably thiazolidinedione class compounds, more prefereably selected from the group consisting of pioglitazone, troglitazone, rosiglitazone and indomethacin, preferably troglitazone and rosiglitazone;

f. bone morphogenetic proteins (BMPs), preferably BMP-2, BMP-4, BMP-7 and BMP-9, preferably BMP-2 and BMP-4.

Some target tissues comprise glandular tissue or are located adjacent to glandular tissue, in particular in the female breasts. It is preferred that the glandular tissue adjacent to or surrounding the target tissue grows together with the adipose tissue so that the result as a whole is more even, natural and aestetically pleasing.

In a more preferred embodiment the composition of the invention is one specifically formulated for the growth of breast target tissue, further comprising at least one glandular growth effector, preferably a mammary glandular growth effector, more preferably a glandular growth factor selected from the group consisting of a. estradiol and estradiol derivatives, preferably selected from the group consisting of estradiol benzoate, estradiol hemihydrate, estradiol acetate, estradiol cypionate, estradiol valerate, ethinyl estradiol and 17β-estradiol, more preferably estradiol and estradiol cypionate, most preferably 17β-estradiol;

b. epidermal growth factor (EGF), vascular endothelial growth factor (VEGF)-A, vascular endothelial growth factor (VEGF)-C, transforming growth factor-α (TGF-α), epiregulin (EPR), epigen, betacellulin (BTC), all neuregulin-1 (NRG1) isoforms, Heregulin (HRG), acetylcholine receptor-inducing activity (ARIA) growth factor, glial growth factor (GGF)), neuregulin-2 (NRG2), neuregulin-3 (NRG3), neuregulin-4 (NRG4), heparin-binding EGF-like growth factor (HB-EGF) and amphiregulin (AR), preferably epidermal growth factor (EGF), transforming growth factor-α (TGF-α), neuregulin-4 (NRG4), heparin-binding EGF-like growth factor (HB-EGF) and amphiregulin (AR), more preferably human epidermal growth factor (EGF);

c. anti-androgens, preferably selected from the group consisting of bicalutamide, nilutamide, spironolactone and flutamide, more preferably spironolactone and flutamide.

In a further preferred embodiment the metabolic lipids for use in the invention comprise fatty acids, preferably fatty acids selected from the group consisting of butanoic acid and longer chain fatty acids, more preferably selected from the group consisting of pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, hexatriacontanoic acid, myristoleic acid, palmitoleic acid, oleic acid, elaidic acid, vaccenic acid, linoleic acid, linoelaidic acid, linolenic acid, preferably a-linolenic acid, arachidonic acid, eicosapentaenoic acid, erucic acid, docosahexanoic acid, stearidonic acid, docosapentaenoic acid, eicosatetraenoic acid and docosahexaenoic acid, more preferably fatty acids selected from the group consisting of octadecanoic acid, dodecanoic acid, hexadecanoic acid and oleic acid, most preferably hexadecanoic acid, octadecanoic acid, and oleic acid.

In a further preferred embodiment the physiologically acceptable, preferably biodegradable CR compounds for use in the invention are selected from the group consisting of poly(lactic-co-glycolic acid) (PLGA), polylactic acid (PLA), polycaprolactone (PCL), poloxamers, polyethylene glycol (PEG)-PLGA co-polymers, combinations of PEG and PLGA, combinations of PLA and PEG, preferably PLA-PEG-PLA, combinations of PLGA and poloxamers, dextran, alginate and polymethacrylate, preferably PLA, PLGA and PEG-PLGA combinations, more preferably PLGA and PLA, most preferably PLGA.

In the following, most preferred but non-limiting embodiments of the compositions of the invention are described.

In a most preferred embodiment the present invention teaches a composition, preferably without fat cell growth effectors or glandular growth effectors, comprising biodegradable poly(lactic-co-glycolic acid) (PLGA) microspheres, hexadecanoic acid and/or oleic acid and optionally vitamin C and/or E, preferably comprising
(i) PLGA with a molecular weight of 21,000 Da and a ratio of lactic acid and glycolic acid of about 1:1,
(ii) hexadecanoic acid and/or oleic acid, preferably associated with albumin and
(iii) vitamin C and/or E.

In a further most preferred embodiment the present invention teaches a composition with at least one fat cell growth effector, comprising biodegradable poly(lactic-co-glycolic acid) (PLGA) microspheres, hexadecanoic acid and/or oleic acid, insulin, FGF-1, rosiglitazone, betamethazone and optionally vitamin C and/or E, preferably comprising
(i) PLGA with a molecular weight of 21,000 Da and a ratio of lactic acid and glycolic acid of about 1:1,
(ii) oleic acid and/or hexadecanoic acid, preferably associated with albumin,
(iii) human recombinant insulin, FGF-1, rosiglitazone, betamethasone and vitamin C and/or E.

In a further most preferred embodiment the present invention teaches a composition, preferably for breast treatment, with at least one fat cell growth effector and at least one glandular growth factor, comprising biodegradable poly(lactic-co-glycolic acid) (PLGA) microspheres, hexadecanoic acid and/or oleic acid, insulin, FGF-1, rosiglitazone, betamethazone, EGF-1, spironolactone, estradiol and optionally vitamin C and/or E, preferably comprising
(i) PLGA with a molecular weight of 21,000 Da and a ratio of lactic acid and glycolic acid of about 1:1,
(ii) hexadecanoic and/or oleic acid, preferably associated with albumin,
(iii) human recombinant insulin, FGF-1, rosiglitazone, betamethasone, EGF-1, spironolactone, estradiol and vitamin C and/or E.

In a further most preferred embodiment the present invention teaches a composition, preferably for facial treatment, with at least one fat cell growth effector and at least one estrogenic growth factor, comprising biodegradable poly(lactic-co-glycolic acid) (PLGA) microspheres, hexadecanoic acid and/or oleic acid, insulin, FGF-1, rosiglitazone, betamethazone, estradiol and optionally vitamin C and/or E, preferably comprising
(i) PGLA with a molecular weight of 21,000 Da and a ratio of lactic acid and glycolic acid of about 1:1,
(ii) oleic acid and/or hexadecanoic acid, preferably associated with albumin,
(iii) human recombinant insulin, FGF-1, rosiglitazone, betamethasone, estradiol and vitamin C and/or E.

The compositions of the invention are for use in therapeutic or cosmetic treatment, and may optionally comprise further physiologically acceptable excipients and diluents.

Therefore, and in a further aspect, the present invention pertains to the use of a composition of the invention for producing a cosmetic or therapeutic composition, preferably for fat tissue expansion or fat tissue repair.

In a preferred embodiment the composition of the invention is for use in fat tissue expansion, preferably fat tissue volume expansion, more preferably for tissues of the face, the buttocks and/or breasts.

In a more preferred embodiment the composition of the invention is for use in the therapeutic or cosmetic treatment of a condition selected from the group consisting of
(i) medical indications selected from the group consisting of body deformities, preferably post-traumatic scars, breast reconstruction and soft tissue depressions; congenital deformities, preferably pectus excavatum deformity, breast assymetry (e.g. Poland syndrome), hemisyndromes (e.g. CLOVE syndrome, Romberg syndrome); deformities near prostheses, recontouring post-radiation thigh defect, HIV lipodystrophy, mild velopharyngeal insufficiency; and
(ii) non-medical indications selected from the group consisting of cosmetic fat tissue augmentation, preferably fat tissue augmentation of breast, buttock, face, genitals, hands and legs, and iatrogenic deformities, preferably peri-prothetic irregularities, liposuction deformities, and implant deformities.

In a most preferred embodiment the composition of the invention is for use in the therapeutic or cosmetic treatment of a medical indication for post-mastectomy breast reconstruction or for breast or buttock augmentation.

In a further most preferred embodiment the composition of the invention is for use in the therapeutic or cosmetic treatment of a condition selected the group consisting of (I) medical indications selected from the group consisting of facial reconstruction after trauma and deformities, preferably acne scars, HIV induced lipodystrophy, scars; and (II) non-medical indications selected from the group consisting of cosmetic facial augmentation, preferably to cheeks, eyebrows, forehead, glabella, lips, Marionette lines, nasolabial folds, nose, periocular wrinkles and sunken eyelid deformity.

A further aspect of the present invention is directed to a method for the therapeutic or cosmetic treatment of a mammal, preferably a human, more preferably a cosmetic or therapeutic treatment of one of the above-cited cosmetic and therapeutic conditions, comprising the steps of
(i) providing a composition of the invention,
(ii) optionally adminstering anesthesia locally to the tissue to be treated,
(iii) injection administration of the composition and preferably injecting the composition while withdrawing the injection needle,
(iv) optionally repeating step (iii) until the entire tissue is treated.

In the following, the invention will be further illustrated by way of specific embodiments, none of which are to be interpreted as limiting the scope of the claims as appended.

FIGURES

FIG. 1 (A) is a schematic drawing of a side view of a blunt-tip cannula insertion into a breast showing that small aliquots of liquid composition according to the invention are released while the needle is continuously withdrawn.

FIG. 1 (B) is a schematic drawing of a top view of a breast where the needle is inserted from either one of two points on the areola margin or one of two points at the inframammary fold in variable directions and planes to achieve a diffuse and even distribution.

The compositions designated oleic acid-PLGA (50:50), oleic acid-PLGA (65:35), oleic acid-PLA (PLA: mol. weight =50,000), heptadecanoic acid-PLGA (50:50), hexadecanoic acid-PLGA (50:50), decanoic acid-PLGA (50:50) and docosanoic acid-PLGA (50:50) were produced according to Example 4.

The control consisted of empty microspheres made according to Example 5.

The composition designated microspheres was produced according to examples 4, 6 and 8.

The composition designated control was produced according to example 5.

FIGS. 6 (A) and (B) show CT scan photographs of inguinal fat pads treated with the PLGA microspheres according to Example 13, 15 days post treatment with PLGA microspheres without (A) and with (B) oleic acid.

EXAMPLE 1

Compositions of the Invention

The ranges cited for each constituent of the below compositions relate to the amounts and activity units of each compound in a composition for treating one tissue area in a patient and it is understood that the amounts and activity units will vary with the patient, the particular target tissue, the tissue surface area and volume, the condition to be treated, the effect to be obtained, etc.

Composition A
(i) 100-200 g biodegradable PLGA microspheres with a molecular weight of 21,000 Da and a ratio of lactic acid and glycolic acid of about 1:1;
(ii) 100-500 g oleic acid and/or hexadecanoic acid associated with albumin and
(iii) 2-20 mg vitamin C and/or E.

Composition A is particularly suited for temporary fat tissue augmentation because it lacks fat cell growth effectors and after some time the augmentation result has passed, e.g. weeks to months, the superfed and volume-augmented cells are likely to use up or to supply the metabolic lipids to other cells. The effect of vitamin E is that it serves as a preservative and anti-oxidant especially for the lipid-based components in the formulation.

Composition B
(i) 100-200 g biodegradable PLGA microspheres with a molecular weight of 21,000 Da and a ratio of lactic acid and glycolic acid of about 1:1;
(ii) 100-500 g oleic acid and/or hexadecanoic acid associated with albumin;
(iii) 50-100 IU human recombinant insulin;
(iv) 200-400 µg FGF-1;
(v) 2-10 mg rosiglitazone;
(vi) 1000-2000 µg betamethasone and
(vii) 2-20 mg vitamin C and/or E.

Composition B is particularly suited for permanent adipose tissue augmentation because it includes fat cell growth factors (iii) to (vi) that stimulate adipogenesis, i.e. the cell differentiation of pre-adipocytes to adipocytes and the proliferation of adipocytes.

Composition C
(i) 100-200 g biodegradable PLGA microspheres with a molecular weight of 21,000 Da and a ratio of lactic acid and glycolic acid of about 1:1;
(ii) 100-500 g oleic acid and/or hexadecanoic acid associated with albumin;
(iii) 50-100 IU human recombinant insulin;
(iv) 200-400 µg FGF-1;

(v) 2-10 mg rosiglitazone;
(vi) 1000-2000 µg betamethasone;
(vii) 200-400 µg EGF-1;
(viii) 50-200 mg spironolactone;
(ix) 2-4 mg 17γ-estradiol and
(x) 2-20 mg vitamin C and/or E.

Composition C is particularly suited for breast adipose tissue augmentation because it includes fat cell growth factors (iii) to (vi) that stimulate adipogenesis and, in addition, the glandular growth effectors (vii) to (ix) that promotes the growth of mammary glands.

Composition D
(i) 100-200 g biodegradable PLGA microspheres with a molecular weight of 21,000 Da and a ratio of lactic acid and glycolic acid of about 1:1;
(ii) 100-500 g oleic acid and/or hexadecanoic acid associated with albumin;
(iii) 1-2 IU human recombinant insulin;
(iv) 4-8 µg FGF-1;
(v) 40-200 mg rosiglitazone;
(vi) 20-140 µg betamethasone;
(vii) 0-4 mg 17γ-estradiol (0 mg for men, 0-1 mg for pre-menopausal women, 2-4 mg for post-menopausal women)
(viii) 2-20 mg vitamin C and/or E.

Composition D is particularly suited for facial adipose tissue augmentation because it includes fat cell growth factors (iii) to (vi) that stimulate adipogenesis and, in addition, estradiol that interacts with the estrogen receptor in the skin resident fibroblasts and stimulates collagen formation.

EXAMPLE 2

Method of the Invention

In the following, two methods for practicing the invention are described.

Method A
(i) providing a composition of the invention, in particular one of compositions A to D,
(ii) application of local anesthesia to the target tissue area, in particular face, breast or buttocks,
(iii) producing 1 mm sized incisions on the target area at regular intervals for crossed and superimposed distribution planes,
(iv) producing multiple and evenly distributed injections with the composition in a syringe equipped with a 15-30 gauge foam tipped needle or a sharp V tipped cannula while withdrawing, thus producing vertical deposits along the injection canal,
(v) repeating step (iv) until the entire target area is evenly covered.

Method B
(i) providing a composition of the invention, in particular one of compositions A to D,
(ii) application of topical or regional anesthesia including nerve blocks to the target tissue area, in particular face, breast or buttocks,
(iii) inserting a 15-30 gauge blunt tip needle of a syringe comprising the composition to an appropriate tissue depth at a primary injection point,
(iv) as the needle is withdrawn, delivering the composition in a slow and continuous manner until the needle is completely removed from the skin or, alternatively, the direction of the needle is continually changed in a radial fashion and new lines are injected without withdrawing until all of the target area is covered,
(v) injecting a series of threads at a secondary point perpendicular to the primary injection point to provide better coverage of larger target areas,
(vi) steps (ii) to (v) may be repeated in multiple target areas, in particular in facial target areas.

EXAMPLE 3

Injection Technique of the Invention

The preferred injection technique for administering the compositions of the invention is similar to the autologous fat transfer techniques used by surgeons and is described with reference to FIGS. 1 (A) and 1 (B).

Figure 1:
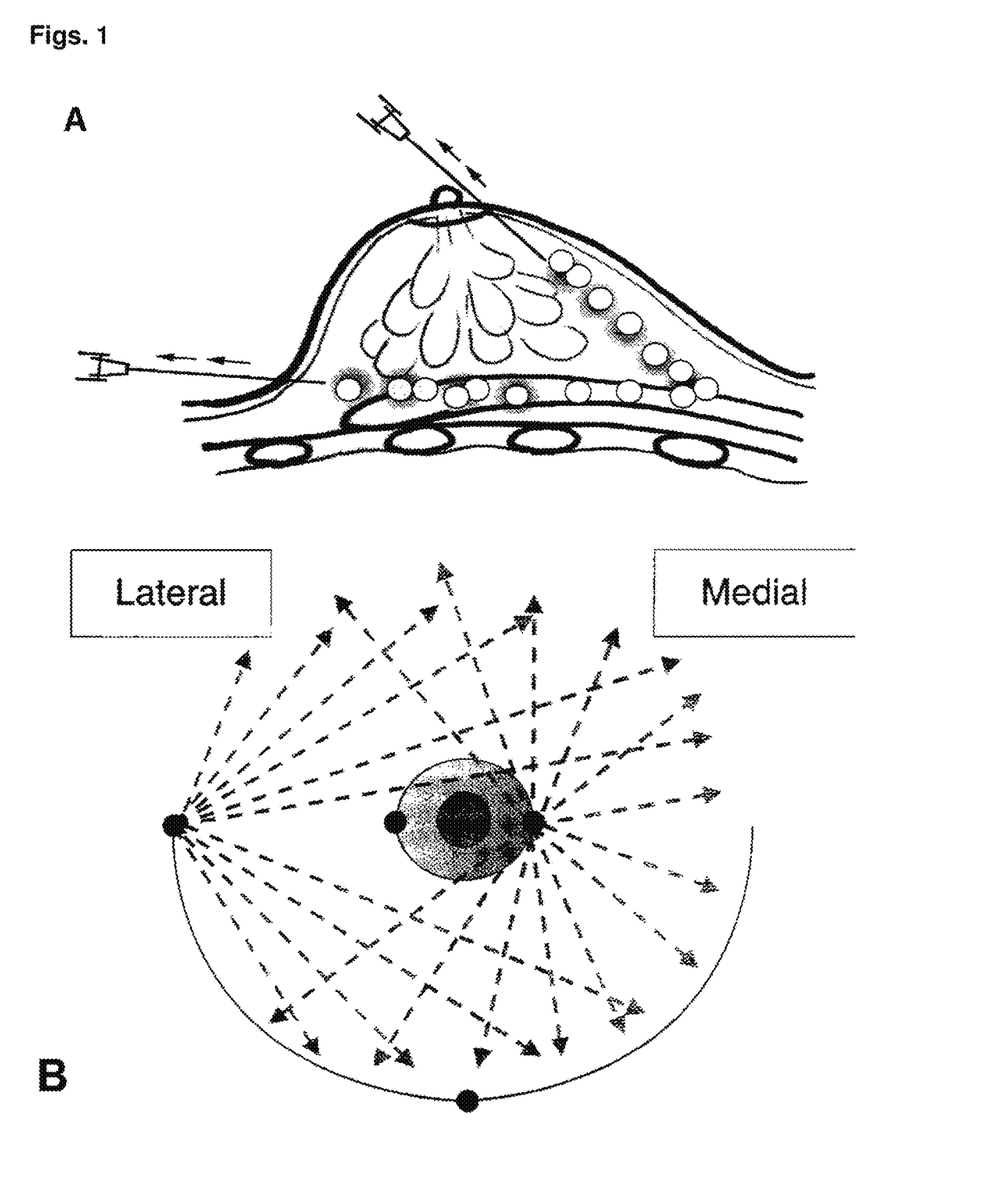

The basic principles behind the above injection technique of FIGS. 1 (A) and (B) is to evenly distribute the inventive composition throughout the target tissue in order to provide for multiple and evenly distributed metabolic lipid deposits controlled in their release by the co-formulated CR compounds to ensure a uniform diffusion of the metabolic lipids and the optional effector compounds throughout the target area. Preferred biodegradable microspheres are similar in shape and size to fat cells.

Preferred injection volumes may vary between 0.1 mL and 500 mL, as these depend on the injection site, patient and surgeon's choice. During the injection session small volumes are released at regular intervals to allow 3-D shaping and to prevent cyst formation. The injection target areas are preferably massaged to ensure an even distribution and to prevent cyst formation as well.

EXAMPLE 4

Synthesis of PLGA-fatty Acids Microspheres

1. Poly (lactic-co-glycolic acid) 50:50 (30,000-60,000) or Poly (lactic-co-glycolic acid) 65:35 (40,000-75,000) or Poly (lactic-co-glycolic acid) 85:15 (50,000-75,000) was obtained from Sigma Aldrich. 200 mg of the polymer was weighed on a balance and dissolved in HPLC grade dichloromethane. This mixture was stirred at 500 RPM
2. After the polymer had completely dissolved 100 µL of the fatty acid of interest (decanoic acid, heptadecanoic acid, hexadecanoic acid, oleic acid, docosanoic acid) was added to the dichloromethane solution while spinning.
3. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with a S 25 N-10 G Dispersing element.
4. The homogenization speed was set at 6000 RPM and while the solution was being homogenized, the dichloromethane solution with the mixture was added to the PVA solution in a drop wise manner.
5. This mixture was allowed to homogenize for 5 min.
6. This homogenized solution was added to 300 mL of 0.5% PVA being stirred at 700 RPM.
7. The solvent was allowed to evaporate for 4 h resulting in the formation of microspheres and their hardening.
8. The PVA solution containing the microspheres was centrifuged at 8000 RPM and washed for 3 consecutive times with double distilled water.
9. The supernatant was collected before the first wash for analysis.

10. The microspheres that were in the pellet were resuspended in 3 mL of double distilled water.
11. These resuspended microspheres were put through freeze drying for 12 h.
12. Microscopy or/and coulter counter was used to determine the size of the microspheres that were between 10-50 microns.
13. The collected supernatant was used to obtain the total amount of fatty acid that was encapsulated. The encapsulation efficiency was between 10-90%.
14. The microsphere powder was resuspended in a 2% solution of carboxyl methyl cellulose (Mw 90,000, Sigma Aldrich) and vortexed vigorously. The solution was vortexed before injecting into mice or introduced into cell culture.

EXAMPLE 5

Synthesis of PLGA Microspheres (Empty)

1. Poly (lactic-co-glycolic acid) 50:50 (30,000-60,000) or Poly (lactic-co-glycolic acid) 65:35 (40,000-75,000) or Poly (lactic-co-glycolic acid) 85:15 (50,000-75,000) was obtained from Sigma Aldrich. 200 mg of the polymer was weighed on a balance and dissolved in HPLC grade dichloromethane. This mixture was stirred at 500 RPM
2. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with a S 25 N-10 G Dispersing element.
3. The homogenization speed was set at 6000 RPM and while the solution was being homogenized, the dichloromethane solution with the mixture was added to the PVA solution in a drop wise manner.
4. This mixture was allowed to homogenize for 5 min.
5. This homogenized solution was added to 300 mL of 0.5% PVA being stirred at 700 RPM.
6. The solvent was allowed to evaporate for 4 h resulting in the formation of microspheres and their hardening.
7. The PVA solution containing the microspheres was centrifuged at 8000 RPM and washed for 3 consecutive times with double distilled water.
8. The microspheres that were in the pellet were resuspended in 3 mL of double distilled water.
9. These resuspended microspheres were put through freeze drying for 12 h.
10. Microscopy or/and coulter counter was used to determine the size of the microspheres that were between 10-50 microns.
11. The microsphere powder was resuspended in a 2% solution of carboxyl methyl cellulose (Mw 90,000, Sigma Aldrich) and vortexed vigorously. The solution was vortexed before injecting into mice.

EXAMPLE 6

Synthesis of PLGA-Dexamethasone Microspheres

1. Poly (lactic-co-glycolic acid) 50:50 (30,000-60,000) or Poly (lactic-co-glycolic acid) 65:35 (40,000-75,000) or Poly (lactic-co-glycolic acid) 85:15 (50,000-75,000)was obtained from Sigma Aldrich. 200 mg of the polymer was weighed on a balance and dissolved in HPLC grade dichloromethane. This mixture was stirred at 500 RPM.
2. After the polymer had completely dissolved, 100 mg of dexamethasone (Sigma Aldrich) was added and completely dissolved.
3. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with an S 25 N-10 G Dispersing element.
4. The homogenization speed was set at 6000 RPM and while the solution was being homogenized, the dichloromethane solution with the mixture was added to the PVA solution in a drop wise manner.
5. This mixture was allowed to homogenize for 5 min.
6. This homogenized solution was added to 300 mL of 0.5% PVA being stirred at 700 RPM.
7. The solvent was allowed to evaporate for 4 h resulting in the formation of microspheres and their hardening.
8. The PVA solution containing the microspheres was centrifuged at 8000 RPM and washed for 3 consecutive times with double distilled water.
9. The microspheres that were in the pellet were resuspended in 3 mL of double distilled water.
10. These resuspended microspheres were put through freeze drying for 12 h.
11. Microscopy or/and coulter counter was used to determine the size of the microspheres that were between 10-50 microns.
12. A sample of microspheres was degraded with a dilute alkali solution, the supernatant was analyzed using a UV transparent plate at 241 nm and compared to a standard curve constructed appropriately. The encapsulation efficiency was about 2-10%.
13. The microsphere powder was resuspended in a 2% solution of carboxyl methyl cellulose (Mw 90,000, Sigma Aldrich) and vortexed vigorously. The solution was vortexed before injecting into mice.

EXAMPLE 7

Synthesis of PLA-fatty Acids Microspheres

1. Poly(L-lactide) (PLA), average $M_n$ 50,000 was obtained from Sigma Aldrich. 200 mg of the polymer was weighed on a balance and dissolved in HPLC grade dichloromethane. This mixture was stirred at 500 RPM.
2. After the polymer had completely dissolved 100 µL of the fatty acid of interest (decanoic acid, heptadecanoic acid, hexadecanoic acid, oleic acid, docosanoic acid) was added to the dichloromethane solution while spinning.
3. A 95 mL 4% solution of polyvinyl alcohol (PVA) ($M_w$ 89,000-98,000, 99+% hydrolyzed) was introduced into a 200 mL beaker and homgeniyed using a IKA T25 digital ultra turrax instrument equipped with an S 25 N-10 G Dispersing element.
4. The homogenization speed was set at 6000 RPM and while the solution was being homogenized, the dichloromethane solution with the mixture is added to the PVA solution in a drop wise manner to form the WOW emulsion.
5. This mixture was allowed to homogenize for 5 min.
6. This homogenized solution was added to 300 mL of 0.5% PVA being stirred at 700 RPM.
7. The solvent was allowed to evaporate for 4 h resulting in the formation of microspheres and their hardening.
8. The PVA solution containing the microspheres was centrifuged at 8000 RPM and washed for 3 consecutive times with double distilled water.

9. The supernatant was collected before the first wash for analysis.
10. The microspheres that were in the pellet were resuspended in 3 mL of double distilled water.
11. These resuspended microspheres were put through freeze drying for 12 h.
12. Microscopy or/and coulter counter was used to determine the size of the microspheres that were between 10-50 microns.
13. The collected supernatant was used to obtain the total amount of fatty acid that is encapsulated. The encapsulation efficiency was between 10-90% with an average of about 45%.
14. The microsphere powder was resuspended in a 2% solution of carboxyl methyl cellulose (Mw 90,000, Sigma Aldrich) and vortexed vigorously. The solution was vortexed before injecting into mice or introduced into cell culture.

EXAMPLE 8

Synthesis of PLGA Microspheres Encapsulating Insulin

1. Poly (lactic-co-glycolic acid) 50:50 (30,000-60,000) or Poly (lactic-co-glycolic acid) 65:35 (40,000-75,000) or Poly (lactic-co-glycolic acid) 85:15 (50,000-75,000)was obtained from Sigma Aldrich.
2. 200 mg of the polymer was weighed on a balance and dissolved in HPLC grade dichloromethane. This mixture was stirred at 500 RPM.
3. Recombinant human Insulin (Sigma Aldrich) was dissolved in 0.1 M dilute HCl solution of pH 2.
4. After the polymer had completely dissolved, the solution was introduced into a Ultra turrax machine (IKA T25 digital ultra turrax instrument equipped with an S 25 N-10 G Dispersing element). The insulin solution equivalent to 50 mg was added drop wise to obtain an water in oil (WO) emulsion.
5. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with an S 25 N-10 G Dispersing element.
6. The homogenization speed was set at 6000 RPM and while the solution was being homogenized, the dichloromethane solution with the mixture is added to the PVA solution in a drop wise manner.
7. This mixture was allowed to homogenize for 5 min.
8. This homogenized solution was added to 300 mL of 0.5% PVA being stirred at 700 RPM.
9. The solvent was allowed to evaporate for 4 h resulting in the formation of microspheres and their hardening.
10. The PVA solution containing the microspheres was centrifuged at 8000 RPM and washed for 3 consecutive times with double distilled water.
11. The supernatant was collected before the first wash for analysis.
12. The microspheres that were in the pellet were resuspended in 3 mL of double distilled water.
13. These resuspended microspheres were put through freeze drying for 12 h.
14. Microscopy or/and coulter counter was used to determine the size of the microspheres that were between 10-50 microns.
15. A portion of the microspheres were degraded using dilute alkali overnight and the supernatant was used to quantify the amount of encapsulated insulin using a BCA assay (Binchoninic acid assay).
16. The microsphere powder was resuspended in a 2% solution of carboxy methyl cellulose (Mw 90,000, Sigma Aldrich) and vortexed vigorously. The solution was vortexed before injecting into mice or introduced into cell culture.

EXAMPLE 9

Synthesis of PEG-PLGA-fatty Acids Microspheres

1. Poly(ethylene glycol) methyl ether-block-poly(lactide-co-glycolide), PEG average $M_n$ 5,000, PLGA $M_n$ 55,000 was obtained from Sigma Aldrich. 200 mg of the polymer was weighed on a balance and dissolved in HPLC grade dichloromethane. This mixture was stirred at 500 RPM.
2. After the polymer had completely dissolved 100 μL of the fatty acid of interest (decanoic acid, heptadecanoic acid, hexadecanoic acid, oleic acid, docosanoic acid) was added to the dichloromethane solution while spinning.
3. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with an S 25 N-10 G Dispersing element.
4. The homogenization speed was set at 6000 RPM and while the solution was being homogenized, the dichloromethane solution with the mixture was added t the PVA solution in a drop wise manner.
5. This mixture was allowed to homogenize for 5 min.
6. This homogenized solution was added to 300 mL of 0.5% PVA being stirred at 700 RPM.
7. The solvent was allowed to evaporate for 4 h resulting in the formation of microspheres and their hardening.
8. The PVA solution containing the microspheres was centrifuged at 8000 RPM and washed for 3 consecutive times with double distilled water.
9. The supernatant was collected before the first wash for analysis.
10. The microspheres that were in the pellet were resuspended in 3 mL of double distilled water.
11. These resuspended microspheres were put through freeze drying for 12 h.
12. Microscopy or/and coulter counter was used to determine the size of the microspheres that were between 10-50 microns.
13. The collected supernatant was used to obtain the total amount of fatty acid that is encapsulated. The encapsulation efficiency was between 10-90%.
14. The microsphere powder was resuspended in a 2% solution of carboxyl methyl cellulose (Mw 90,000, Sigma-Aldrich) and vortexed vigorously. The solution was vortexed before injecting into mice or introduced into cell culture.

EXAMPLE 10

Synthesis of PEG-PLGA-PEG Fatty Acids Microspheres

1. Poly(lactide-co-glycolide)-block-poly(ethylene glycol)-block-poly(lactide-co-glycolide) average $M_n$ (1100-1000-1100) was obtained from Sigma Aldrich. 200 mg of the polymer was weighed on a balance and dissolved in HPLC grade dichloromethane. This mixture was stirred at 500 RPM.
2. After the polymer had completely dissolved 100 µL of the fatty acid of interest (decanoic acid, heptadecanoic acid, hexadecanoic acid, oleic acid, docosanoic acid) was added to the dichloromethane solution while spinning.
3. A 95 mL 4% solution of polyvinyl alcohol (PVA) ($M_w$ 89,000-98,000, 99+% hydrolyzed) was introduced into a 200 mL beaker and homogenized using a IKA T25 digital ultra turrax instrument equipped with an S 25 N-10 G Dispersing element.
4. The homogenization speed was set at 6000 RPM and while the solution was being homogenized, the dichloromethane solution with the mixture was added to the PVA solution in a drop wise manner.
5. This mixture was allowed to homogenize for 5 min.
6. This homogenized solution was added to 300 mL of 0.5% PVA being stirred at 700 RPM.
7. The solvent was allowed to evaporate for 4 h resulting in the formation of microspheres and their hardening.
8. The PVA solution containing the microspheres was centrifuged at 8000 RPM and washed for 3 consecutive times with double distilled water.
9. The supernatant was collected before the first wash for analysis.
10. The microspheres that were in the pellet were resuspended in 3 mL of double distilled water.
11. These resuspended microspheres were put through freeze drying for 12 h.
12. Microscopy or/and coulter counter was used to determine the size of the microspheres that were between 10-50 microns.
13. The collected supernatant was used to obtain the total amount of fatty acid that was encapsulated. The encapsulation efficiency is in between 10-90%.
14. The microsphere powder was resuspended in a 2% solution of carboxyl methyl cellulose (Mw 90,000, Sigma-Aldrich) and vortexed vigorously. The solution was vortexed before injecting into mice or introduced into cell culture.

EXAMPLE 11

In Vitro Uptake of Different CR Compound/Fatty Acid Compositions

3T3-L1 is a cell line derived from (mouse) 3T3 cells that is commonly used in biological research on adipose tissue. This cell line is generally accepted as a predictable cell model for fat cell research. 3T3-L1 cells (P9) (ATCC, Germany) were seeded at 25000 cells per well in a 96 well plate. These cells were allowed to attain confluence over 2 days. The medium was changed from DMEM (10% serum+Streptomycin (100 U)+Penicillin (0.1 mg/ml)) (Everything sourced from Gibco, Switzerland) to DMEM (10% serum+insulin+dexamethasone Streptomycin (100 U)+Penicillin (0.1 mg/ml)). After two days this medium was changed to DMEM (10% serum+Insulin Streptomycin (100 U)+Penicillin(0.1 mg/ml)+X) Here X represents either oleic acid, heptadecanoic acid, hexadecanoic acid, decanoic acid and docosanoic acid according to Example 4. An oleic acid-PLA composition was produced according to Example 7. The fatty acids were added to each well at a concentration of 20 µM. In the case of the control, empty microspheres were added at the same approximate concentration of polymer (5 mg/well), Example 5. In all cases, the microsphere size range was maintained above 10 microns. The medium was changed every three days with a fresh supplement of the respective microspheres. The cells were lysed using 1% Triton X-100 and the triglyceride levels were measured via an assay. The statistics were performed using a one way ANOVA with a Tukey Post Test.

Figure 2:
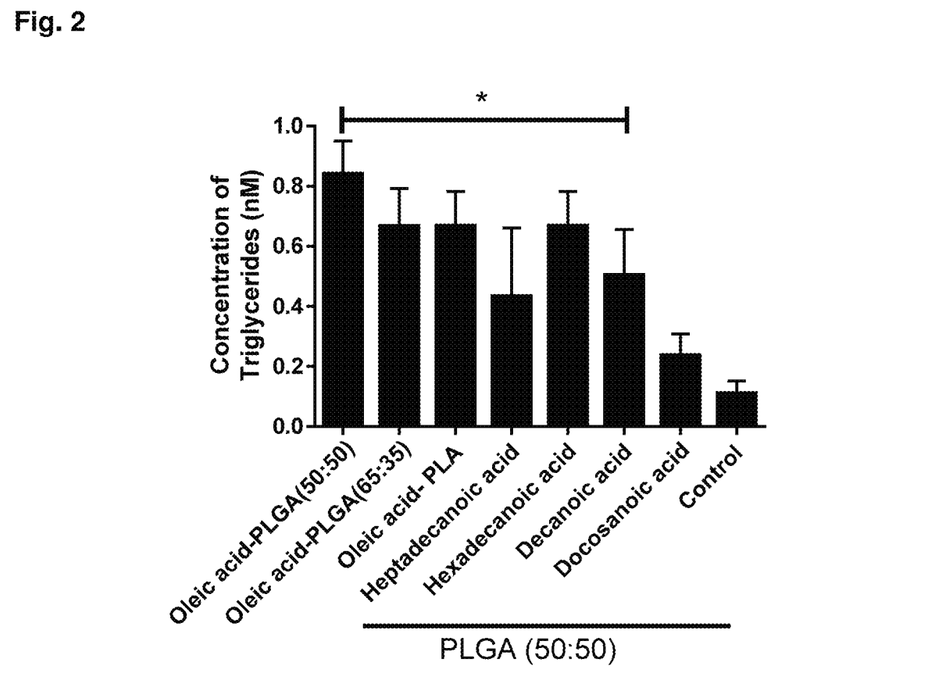
FIG. 2 shows a graph depicting the concentration of triglycerides taken up by 3T3-L1 cells (P9) upon incubation together with a number of different fatty acid-CR compound compositions according to the invention, wherein the CR compounds control the release of the co-formulated fatty acids. The asterisk represents statistical significance with reference to the control. The detailed procedure was according to Example 11.
Figure 3:
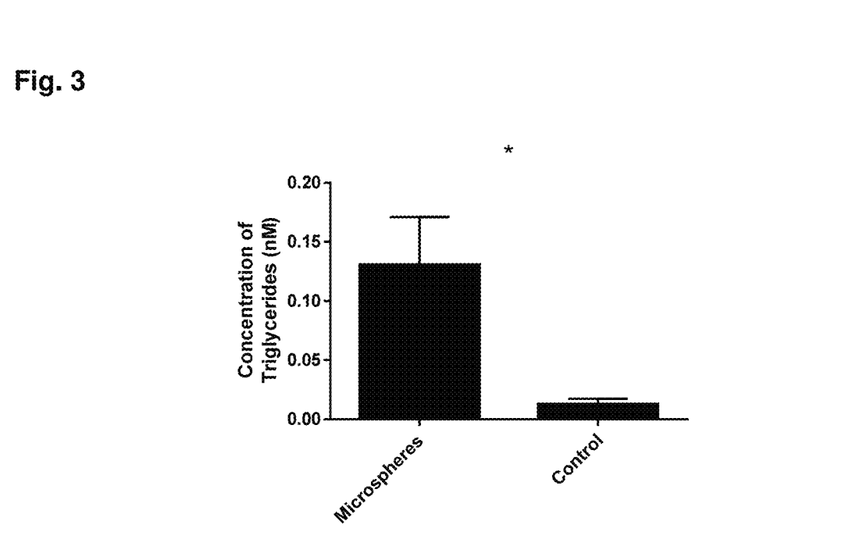
FIG. 3 shows a graph depicting the concentration of triglycerides in 3T3-L1 cells (P9) wherein undifferentiated 3T3-L1 cells were treated with PLGA-Insulin+PLGA-Dexamethasone+PLGA-Oleic acid and compared against cells treated with cell culture medium+empty PLGA microspheres (control). After the two days of introducing this each of the groups was treated with medium that has encapsulated insulin and oleic acid. The detailed procedure is as per Example 12.
Figure 4:
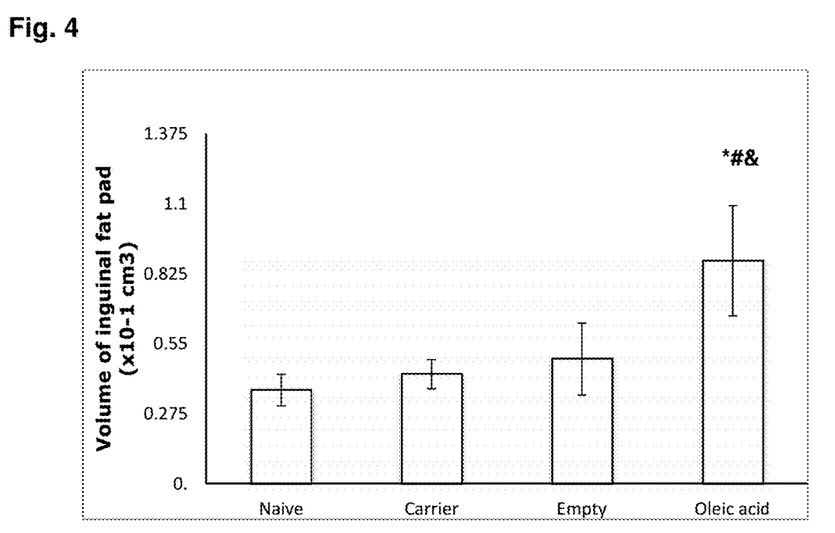
FIG. 4 shows a graph allocating the volume of inguinal fat pads of Balb-c nude mice without treatment (naive, control), with CMC carrier injected (control), with empty microspheres according to example 5 injected (empty, control), and with oleic acid-comprising microspheres according to Example 4 and carrier injected (oleic acid) into the inguinal fat pad 15 days after treatment. *#$ represents statistical significance as compared to control.
Figure 5:
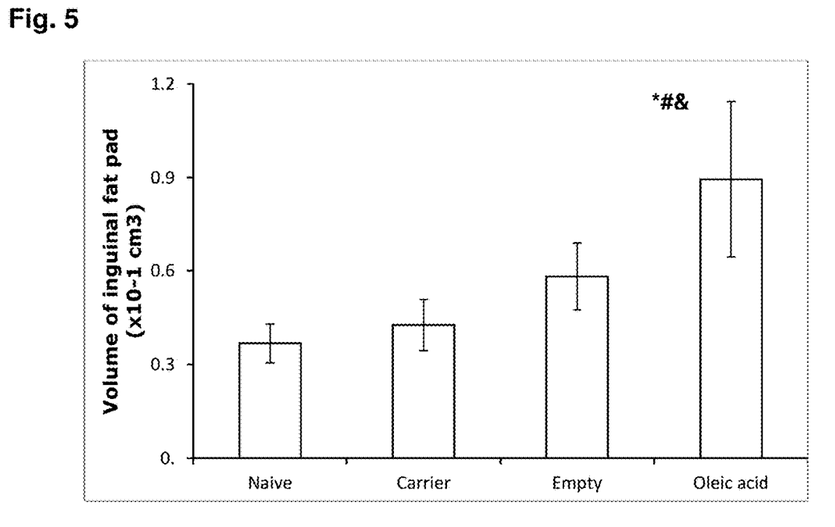
FIG. 5 shows a graph allocating the volume of inguinal fat pads of Balb-c nude mice without treatment (naive, control), with CMC carrier injected (control), with empty microspheres according to Example 5 injected (empty, control), and with oleic acid-comprising microspheres according to Example 4 and carrier injected (oleic acid) into the inguinal fat pad 30 days after treatment. *#$ represents statistical significance as compared to control.
Figure 6:
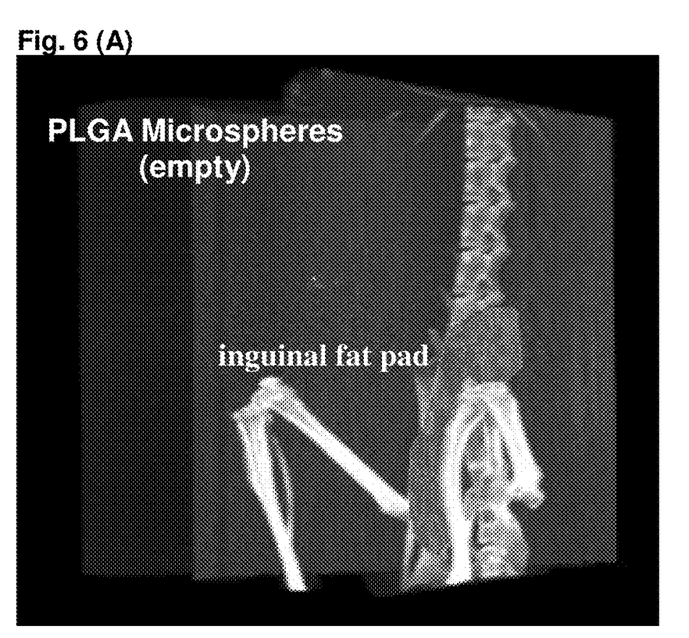

The results obtained and represented by FIG. 2 demonstrate that compositions according to the present invention, i.e. compositions comprising metabolic fatty acids of different types as well as CR compounds of different types with the CR compounds controlling the release of the fatty acids, lead to a significant increase of triglycerides in adipose model cells, thus proving the controlled uptake and incorporation of fatty acids from CR compositions into cellular triglycerides. This expansion in triglyceride level is independent of the composition and type of the CR compound, as well as of the type, carbon chain length and saturation degree of physiologically relevant fatty acids.

EXAMPLE 12

In Vitro Influence of CR Controlled Insulin and Dexamethasone on Triglyceride Concentration 3T3-L1 cells (P9) were seeded at 25000 cells per well in a 96 well plate. These cells were allowed to attain confluence over 2 days. The medium was changed from DMEM (10% serum) to DMEM (10% serum+insulin+dexamethasone+Oleic acid+Streptomycin (100 U)+Penicillin (0.1 mg/ml)). The insulin, dexamethasone and oleic acid were encapsulated in PLGA microspheres of 50:50 composition as according to Examples 4, 6 and 8. After two days this medium was changed to DMEM (10% serum+insulin+Oleic acid+Streptomycin (100 U)+Penicillin (0.1 mg/ml)) both the oleic acid and insulin were in separate microspheres according to examples 4 and 8. In the case of the control, empty microspheres were added at the same approximate concentration of polymer (5 mg/well). In all cases the microsphere size range was maintained above 10 microns. The medium was changed every three days with a fresh supplement of microspheres either with oleic acid and insulin in all cases. The cells were lysed using Triton X-100 on day 8 and the triglyceride levels were measured via an assay. The statistics were performed using a one way ANOVA with a Tukey Post Test.

This experiment showed that our microspheres that contain dexamethasone and insulin separately along with oleic acid microspheres induce differentiation of 3T3-L1 cells and the subsequent storage of triglycerides where as the control has very little differentiation thus no triglyceride storage. This experiment demonstrates that our combination of CR compounds along with insulin and dexamethasone in separate micro particles can induce differentiation of undifferentiated fat cells and their subsequent enhancement in volume.

EXAMPLE 13

In Vivo Animal Tests

The lyophilized microspheres that were made as per example 4 (approximately 25 mg of polymer/mouse and 22.5 mg of oleic acid/mouse were re-suspended in 50-200 cP, 2% in $H_2O$ solution of 90 KDa sodium carboxy methyl cellulose with a degree of polymerization of 400 and degree of substitution at 0.65-0.9 (Referred to as CMC from here on) overnight and vigorously vortexed before use. The encapsulation efficiency of oleic acid was approximately 45% (45 mg of oleic acid per 100 mg of oleic acid-microsphere composition). The poly lactic acid—glycolic acid polymer was used at a 50:50 ratio (30,000-60,000) yielding microspheres of diameter 10-50 microns. 2 month old Balb-c nude mice were used for experiments, each group had 5 mice that were sourced from Charles Rivers labs, Italy. These mice were acclimatized to the animal facility for a period of 30 days to avoid secondary effects due to stress. Oleic acid was used at a cell culture grade that was sterile.

The left inguinal fat pad volume was quantified using CT scanning at 15 and 30 days after injection. 50 mg of corresponding microsphere composition was injected into each inguinal fat pad with CMC as carrier corresponding to a total volume of 100 µl per fat pad. A 22 G needle was used for the injection. The mice were anaesthetized using 3% isoflurane. The inguinal fat pad was accessed through the ventral surface. The microspheres were injected while the needle was slowly withdrawn so as to have an even distribution of the injection content within the fat pad.

Oleic acid loaded microspheres clearly enhance the volume of the inguinal fat pad 15 days after injection in a nude mouse as assessed by CT scanning. This animal experiment clearly demonstrates that CR compound/metabolic lipid compositions according to the invention result in a controlled and lasting uptake of the metabolic lipids for significantly and homogeneously expanding the fat cell tissue in the vicinity of these compositions.

The invention claimed is:

1. A method for the therapeutic or cosmetic treatment of a mammal, comprising the steps of:
   (I) providing a composition comprising:
      (a) physiologically acceptable, metabolic lipids, and
      (b) physiologically acceptable controlled release (CR) compounds,
      wherein the lipids are cell-free and the CR-compounds release the metabolic lipids over a delayed time period under physiological conditions; and
   (II) administering the composition via injection; and
   (III) releasing the metabolic lipids over the delayed time period,
   wherein the therapeutic treatment is a treatment of a medical indication selected from the group consisting of body deformities, post-traumatic scars, soft tissue depressions, congenital deformities, pectus excavatum deformity, breast assymmetry, Poland syndrome, hemi-syndromes, CLOVE syndrome, Romberg syndrome, deformities near prostheses, recontouring post-radiation thigh defect, HIV lipodystrophy, mild velopharyngeal insufficiency, post-mastectomy breast reconstruction, facial reconstruction after trauma and deformities, acne scars, HIV induced lipid dystrophy, and scars.

2. The method according to claim 1, wherein step (II) is repeated until an entire tissue intended for therapeutic or cosmetic treatment is treated.

3. The method according to claim 1, further comprising the step of administering anesthesia locally to a site of a tissue to be treated.

4. The method according to claim 1, wherein step (II) is executed by injecting the composition while withdrawing an injection needle.

5. The method according to claim 1, wherein the cosmetic treatment is at least one of: fat tissue expansion, fat tissue volume expansion, fat tissue augmentation, facial augmentation to cheeks, facial augmentation to eyebrows, facial augmentation to forehead, facial augmentation to glabella, facial augmentation to lips, facial augmentation to Marionette lines, facial augmentation to nasolabial folds, facial augmentation to nose, facial augmentation to periocular wrinkles, or facial augmentation to sunken eyelid deformity.

6. The method according to claim 1, wherein the CR-compounds release the metabolic lipids over a delayed time period selected from 7 days to 12months, 30 to 90 days, 50 to 70 days, and over about 60 days.

7. The method according to claim 1, wherein the composition further comprises at least one fat cell growth effector.

8. The method according to claim 7, wherein the at least one fat cell growth effector is at least one of: insulin, insulin growth factor binding proteins 1 (IGFBP 1), IGFBP 2, IGFBP 3, IGFBP 4, IGFBP 5, IGFBP 6, IGFBP 7, insulin growth factor 1 (IGF-1), IGF-2, fibroblast growth factors 1 (FGF-1), FGF-2, FGF-10, FGF-21, glucocorticoids, cyclic adenosine monophosphate (cAMP) activators, peroxisome proliferator-activated receptor γ2 (PPARγ2) agonists, thiazolidinedione class compounds, bone morphogenetic proteins 2 (BMP-2), BMP-4, BMP-7, or BMP-9.

9. The method according to claim 1, wherein the composition further comprises at least one glandular growth effector.

10. The method according to claim 9, wherein the at least one glandular growth effector is selected from the group consisting of estradiol and estradiol derivatives.

11. The method according to claim 1, wherein the metabolic lipids comprise fatty acids.

12. The method according to claim 11, wherein the fatty acids are selected from the group consisting of butanoic acid and longer chain fatty acids, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, hexatriacontanoic acid, myristoleic acid, palmitoleic acid, oleic acid, elaidic acid, vaccenic acid, linoleic acid, linoelaidic acid, α-linolenic acid, arachidonic acid, eicosapentanoic acid, erucic acid, docosahexanoic acid, stearidonic acid, docosapentanoic acid, eicosatetranoic acid and docosahexanoic acid.

13. The method according to claim 1, wherein at least one of the physiologically acceptable controlled release (CR) compounds is biodegradable.

14. The method according to claim 1, wherein the physiologically acceptable, controlled release (CR) compounds are selected from the group consisting of poly(lactic-co-glycolic acid) (PLGA), polylactic acid (PLA), polycaprolactone (PCL), poloxamers, polyethylene glycol (PEG)-PLGA co-polymers, combinations of PEG and PLGA, combinations of PLA and PEG, PLA-PEG-PLA, combinations of PLGA and poloxamers, dextran, alginate and polymethacrylate.

15. The method according to claim 1, wherein the composition comprises:
   (i) biodegradable poly(lactic-co-glycolic acid) (PLGA) microspheres; and
   (ii) oleic acid and/or hexadecanoic acid.

16. The method according to claim 15, wherein the composition further comprises vitamin E.

17. The method according to claim 15, wherein the composition comprises:

PLGA with a molecular weight of 21,000 Da and a ratio of lactic acid and glycolic acid of about 1:1;
(ii) oleic acid and/or hexadecanoic acid; and
(iii) vitamin E.

18. The method according to claim 15, wherein the composition comprises:
   (i) biodegradable poly(lactic-co-glycolic acid) (PLGA) microspheres;
   (ii) oleic acid and/or hexadecanoic acid; and
   (iii) at least one of insulin, FGF-1, rosiglazone, or betamethazone.

19. The method according to claim 15, wherein the composition comprises:
   (i) PLGA with a molecular weight of 21,000 Da and a ratio of lactic acid and glycolic acid of about 1:1;
   (ii) oleic acid and/or hexadecanoic acid;
   (iii) at least one of human recombinant insulin, FGF-1, rosiglitazone, or betamethasone; and
   (iv) vitamin E.

20. The method according to claim 15, wherein the composition comprises:
   (i) biodegradable poly(lactic-co-glycolic acid) (PLGA) microspheres;
   (ii) oleic acid and/or hexadecanoic acid; and
   (iii) at least one of insulin, FGF-1, rosiglazone, betamethazone, EGF-1, spironolactone, or estradiol.

21. The method according to claim 15, wherein the composition comprises:
   (i) PLGA with a molecular weight of 21,000 Da and a ratio of lactic acid and glycolic acid of about 1:1;
   (ii) oleic acid and/or hexadecanoic acid;
   (iii) at least one of human recombinant insulin, FGF-1, rosiglitazone, betamethasone, EGF-1, spironolactone, or estradiol; and
   (iv) vitamin E.

22. The method according to claim 15, wherein the composition comprises:
   (i) biodegradable poly(lactic-co-glycolic acid) (PLGA) microspheres;
   (ii) oleic acid and/or hexadecanoic acid; and
   (iii) at least one of insulin, FGF-1, rosiglazone, betamethazone, or estradiol.

23. The method according to claim 15, wherein the composition comprises:
   (i) PLGA with a molecular weight of 21,000 Da and a ratio of lactic acid and glycolic acid of about 1:1;
   (ii) oleic acid and/or hexadecanoic acid;
   (iii) at least one of human recombinant insulin, FGF-1, rosiglitazone, betamethasone, or estradiol; and
   (iv) vitamin E.

24. The method according to claim 1, wherein the composition comprises hexadecanoic acid associated with albumin.

25. The method according to claim 15, wherein the composition comprises hexadecanoic acid associated with albumin.

26. The method according to claim 1, wherein the cosmetic treatment is at least one of: fat tissue volume expansion for tissues of the face, fat tissue volume expansion for tissues of the buttocks, fat tissue volume expansion for tissues of the breasts, fat tissue augmentation of breast, fat tissue augmentation of buttock, fat tissue augmentation of face, fat tissue augmentation of genitals, fat tissue augmentation of hands, fat tissue augmentation of legs, fat tissue augmentation of iatrogenic deformities, fat tissue augmentation of peri-prothetic irregularities, fat tissue augmentation of liposuction deformities, or fat tissue augmentation of implant deformities.

27. The method according to claim 7, wherein the at least one fat cell growth effector is at least one of: cortisol, cortisone, prednisone, prednisolone, triamcinolone, methylprednisolone, dexamethasone, betamethasone, aminophylline, pentoxyfilline, theophylline, isobutyl-methylxanthine (IBMX), forskolin, dehydroabietic acid (DAA), pioglitazone, troglitazone, rosiglitazone, or indomethacin.

* * * * *